United States Patent [19]

Schwarzenbach et al.

[11] 3,959,413

[45] May 25, 1976

[54] BICYCLIC PHOSPHITES

[75] Inventors: Kurt Schwarzenbach, Pfeffingen, Switzerland; Bernard Gilg, Saint-Louis, France; Heimo Brunetti, Reinach; Helmut Müller, Binningen, both of Switzerland

[73] Assignee: Ciba-Geigy Corporation, Ardsley, N.Y.

[22] Filed: June 27, 1974

[21] Appl. No.: 483,592

[30] Foreign Application Priority Data

July 18, 1973 Switzerland................ 10478/73

[52] U.S. Cl. ................ 260/927 R; 260/937; 260/45.7 R
[51] Int. Cl.² ........................ C07C 9/15
[58] Field of Search ............ 260/927 R, 937

[56] References Cited

UNITED STATES PATENTS

| | | | |
|---|---|---|---|
| 3,155,703 | 11/1964 | Emmons et al. | 260/937 |
| 3,155,705 | 11/1964 | Emmons et al. | 260/937 |
| 3,168,549 | 2/1965 | Rätz | 260/937 |
| 3,607,990 | 9/1971 | Giollto et al. | 260/971 |
| 3,808,296 | 4/1974 | Brunetti | 260/937 X |

FOREIGN PATENTS OR APPLICATIONS 1,171,474  11/1969  United Kingdom........ 260/937

*Primary Examiner*—Anton H. Sutto
*Attorney, Agent, or Firm*—Luther A. R. Hall

[57] ABSTRACT

Bicyclic phosphites are used alone or in combination with other stabilisers for stabilising polyolefines.

3 Claims, No Drawings

BICYCLIC PHOSPHITES

The subject of the present invention is the use of bicyclic phosphites for stabilising polyolefines under the conditions of moulding or processing.

During their production and processing into injection moulded articles, sheets, films or fibres, polyolefines are normally exposed for a short time to temperatures between 200° and 300°C. These temperatures must naturally be far above the melting range of the polymer materials mentioned. Especially in the presence of traces of atmospheric oxygen, such a heat treatment leads to various thermal and oxidative degradation reactions which manifest themselves in an alteration of the flow properties of the molten polymers and in a deterioration of the use properties of the finished articles.

For stabilising polyolefines against degradation under the conditions of moulding and processing, various phosphorus compounds are already known, amongst others bicyclic compounds in which phosphorus is the bridgehead atom. It is also known to use this group of bicyclic compounds as additives in polyvinyl chloride. A description is given both of a plasticising action and also a stabilising action against discolouration under the conditions of dry heat treatment in a circulating air oven at relatively low temperatures below the melting ranges of the polymers used. Such a stabilising effect in polyvinyl chloride is, however, not limited to bicyclic phosphorus compounds, but is observed in phosphites generally.

It has now been found, surprisingly, that the compounds of the formula I

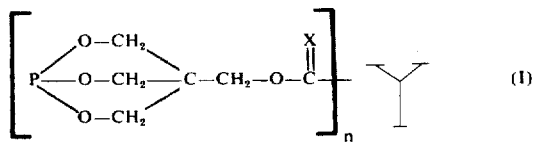

wherein $n$ denotes 1, 2 or 3, Y denotes, if $n$ is equal to 1, a straight-chain or branched alkyl group, an alkenyl group, a cycloalkyl group, an aralkyl group, the phenyl group, a phenyl group substituted by 1 to 3 alkyl groups, a hydroxyphenyl group, a phenyl group substituted by 1 or 2 chlorine atoms, an alkoxyphenyl group, an acyloxyphenyl group, a carbalkoxyphenyl group or a naphthyl group; a straight-chain or branched alkylamino group, a cycloalkylamino group, an aralkylamino group, the anilino group, an anilino group substituted by 1 or 2 chlorine atoms, an alkylanilino group or a naphthylamino group or, if $n$ is equal to 2, a direct bond, a straight-chain or branched alkylene group, a phenylene group, a naphthylene group, a straight-chain or branched alkylenediamino group, a phenylenediamino group which is optionally substituted by an alkyl group, a naphthylenediamino group, the diphenylmethane-4,4'-diamino group or the radical

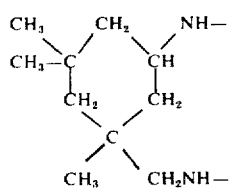

or, if $n$ is equal to 3, a straight-chain or branched alkanetriyl group, an aryltriyl group, a straight-chain or branched alkanetriamino group, or an arylenetriamino group, and X denotes oxygen or sulphur, are stabilisers for homopolymeric or copolymeric polyolefines with an action better than the action of compounds which are similar to the abovementioned group.

Preferably, compounds of the formula I are used in which $n$ denotes 1 or 2, Y denotes, if $n$ is equal to 1, alkyl with 1 to 21 carbon atoms, alkenyl with 2 to 17 carbon atoms, cyclohexyl, benzyl, phenyl, hydroxyphenyl, chlorophenyl, dichlorophenyl, alkylphenyl with 7–14 carbon atoms, alkoxyphenyl with 7–24 carbon atoms, acyloxyphenyl with 8–24 carbon atoms, carbalkoxyphenyl with 8–25 carbon atoms, α-naphthyl or β-naphthyl; alkylamino with 1–18 carbon atoms, cyclohexylamino, benzylamino, anilino, chloroanilino, dichloroanilino, alkylanilino with 7–10 carbon atoms or naphthylamino or, if $n$ is equal to 2, a direct bond, alkylene with 1–8 carbon atoms, phenylene or naphthylene: alkylenediamino with 2–9 carbon atoms, phenylenediamino, toluylenediamino, naphthylenediamino, diphenylmethane-4,4'-diamino or the radical

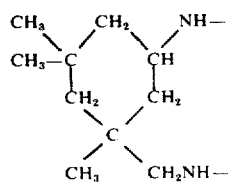

and X denotes oxygen or sulphur.

Particularly preferential use is made of compounds of the formula I in which $n$ denotes 1, Y denotes alkyl with 1–17 carbon atoms, cyclohexyl, benzyl, phenyl, alkylphenyl with 7–14 carbon atoms, alkoxyphenyl with 7–24 carbon atoms, acyloxyphenyl with 8–24 carbon atoms, carbalkoxyphenyl with 8–25 carbon atoms, α-naphthyl, β-naphthyl, alkylamino with 1–18 carbon atoms, cyclohexylamino, anilino, chloroanilino or naphthylamino, and X denotes oxygen, or of compounds of the formula I in which $n$ denotes 1 or 2, Y denotes, if $n$ is equal to 1, alkyl with 4 to 17 carbon atoms, cyclohexyl, benzyl, phenyl, chlorophenyl, alkylphenyl with 7–11 carbon atoms, alkoxyphenyl with 7–14 carbon atoms, α-naphthyl or β-naphthyl; alkylamino with 1–4 carbon atoms or anilino, or, if $n$ is equal to 2, alkylene with 4 carbon atoms, alkylenediamino with 6–9 carbon atoms, diphenylmethane-4,4'-diamino or the radical

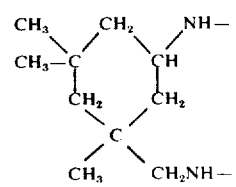

and X denotes oxygen.

The compounds of the formula I are in part known. New compounds of the formula I are those in which $n$ denotes 1, 2 or 3, Y denotes, if n is equal to 1, a straight-chain or branched alkylamino group, a cycloalkylamino group, an aralkylamino group, the anilino group, an anilino group substituted by 1 or 2 chlorine atoms, an alkylanilino group or a naphthylamino group, or, if n is equal to 2, a straight-chain or branched alkylenediamio group, a phenyldiamino group which is optionally substituted by an alkyl group, a naphthylenediamino group, the diphenylmethane-4,4'-diamino group or the radical

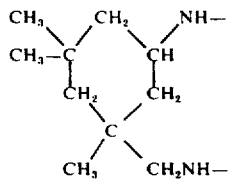

or, if n is equal to 3, a straight-chain or branched alkanetriamino group or an arylenetriamino group, and X denotes oxygen or sulphur.

Amongst the new compounds preference attaches to those of the formula I wherein n denotes 1 or 2, Y denotes, if n is equal to 1, alkylamino with 1–18 carbon atoms, cyclohexylamino, benzylamino, anilino, chloroanilino, dichloroanilino, alkylanilino with 7–10 carbon atoms or naphthylamino, or, if n is equal to 2, alkylenediamino with 2–9 carbon atoms, phenylenediamino, toluylenediamino, naphthylenediamino, diphenylmethane-4,4'-diamino or the radical

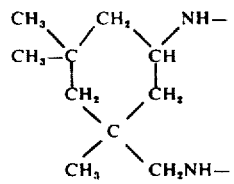

and X denotes oxygen or sulphur.

Amongst the new compounds particular preference attaches to those of the formula I wherein n denotes 1, Y denotes alkylamino with 1–18 carbon atoms, cyclohexylamino, anilino, chloroanilino or naphthylamino and X denotes oxygen, or to compounds of the formula I wherein n denotes 1 or 2, Y denotes, if n is equal to 1, alkylamino with 1–4 carbon atoms or anilino, or, if n is equal to 2, alkylenediamino with 6–9 carbon atoms, diphenylmethane-4,4'-diamino or the radical

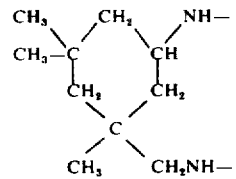

and X denotes oxygen.

In accordance with the definition of the compounds of the formula I, Y can have, for example, the following meaning:

A straight-chain or branched alkyl group, such as methyl, ethyl, isopropyl, n-butyl, sec.-butyl, tert.-butyl, n-amyl, tert.-amyl, sec.-amyl, 2,2-dimethylpropyl, hexyl, octyl, tert.-octyl, 1-methyl-1-ethyl-amyl, decyl, dodecyl, tetradecyl or octadecyl, a cycloalkyl group, such as, for example, cyclohexyl, α-methylcyclohexyl or cyclooctyl, an alkenyl group, such as vinyl, propenyl, butenyl, pentenyl, hexenyl, octenyl, decenyl, tetracenyl or octadecenyl, an aralkyl group, such as benzyl, α-phenylethyl or α,α-dimethylbenzyl, a phenyl group substituted by 1 to 3 alkyl groups, it being possible for the alkyl groups to be methyl, ethyl, iso-propyl, butyl, sec.-butyl, tert.-butyl, amyl, tert.-amyl, sec.-amyl, hexyl, octyl or tert.-octyl, a hydroxyphenyl group, such as 2-hydoxyphenyl, 3-hydroxyphenyl or 4-hydroxyphenyl, a phenyl group substituted by 1 or 2 chlorine atoms, such as 2-chlorophenyl, 3-chlorophenyl, 4-chlorophenyl or 2,4-dichlorophenyl, an alkoxyphenyl group wherein the alkoxy group can be methoxy, ethoxy, propoxy, butoxy, octoxy or octadecyloxy, an acyloxyphenyl group, wherein "acyl" can be the radical of an aliphatic or aromatic carboxylic acid, for example of an alkanoic acid, such as acetic acid, propionic acid, caproic acid, lauric acid or stearic acid or an unsubstituted or substituted benzoic acid, such as benzoic acid, p-tert.butylbenzoic acid or p-tert.-octylbenzoic acid, a carbalkoxyphenyl group, wherein carbalkoxy can be carbomethoxy, carbobutoxy, carbo-2-ethylhexoxy, carbododecyloxy or carbooctadecyloxy, a naphthyl group, such as the α-naphthyl group or the β-naphthyl group, a straight-chain or branched alkylamino group, such as methylamino, ethylamino, iso-propylamino, butylamino, sec.-butylamino, tert.-butylamino, amylamino, tert.-amylamino, sec.-amylamino, hexylamino, octylamino, tert.-octylamino, decylamino, dodecylamino, tetradecylamino or octadecylamino, a cycloalkylamino group, such as, for example, cyclohexylamino or cyclooctylamino, an aralkylamino group, such as benzylamino, an alkylanilino group, wherein the alkyl group can be methyl, ethyl, iso-propyl, butyl, sec.-butyl, tert.-butyl, amyl, tert.-amyl, sec.-amyl, hexyl, octyl or tert.-octyl, an anilino group substituted by 1 or 2 chlorine atoms, such as 2-chloroanilino, 3-chloroanilino, 4-chloroanilino or 2,4-dichlo dichloroanilino, a naphthylamino group, such as α-naphthylamino or β-naphthylamino, a straight-chain or branched alkylene group, such as ethylene, propylene, trimethylene, tetramethylene, hexamethylene, octamethylene, decamethylene or octadecamethylene, a phenylene group, such as o-phenylene, m-phenylene or p-phenylene, a naphthylene group, such as 1,2-naphthylene or 2,6-naphthylene, a straight-chain or branched alkylenediamino group such as ethylenediamino, propylenediamino, trimethylenediamino, tetramethylenediamino, hexamethylenediamino, octamethylenediamino, decamethylenediamino or octadecamethylenediamino, a phenylenediamino group, such as o-phenylenediamino, m-phenylenediamino or p-phenylenediamino, a phenylenediamino group substituted by an alkyl group, it being possible for alkyl to be methyl, ethyl, iso-propyl, butyl, sec.-butyl, tert.-butyl, amyl, tert.-amyl, sec.-amyl, hexyl, octyl or tert.-octyl, or a naphthylenediamino group, such as 2,6 -naphthylenediamino.

Examples of compounds of the formula I are: acetic acid 1-phospha-2,6,7-trioxabicyclo[2,2,2]oct-4-yl-methyl ester, behenic acid -phospha-2,6,7-trioxabicyclo[2,2,2]oct-4-yl-methyl ester, acrylic acid 1-phospha-2,6,7-trioxabicyclo[2,2,2]oct-4-yl-methyl ester, oleic acid 1-phospha-2,6,7-trioxabicyclo[2,2,2]oct- 4-yl-methyl ester, cyclohexanecarboxylic acid 1-phospha-2,6,7-trioxabicyclo[2,2,2]oct-4-yl-methyl ester, p-hydroxybenzoic acid 1-phospha-2,6,7-trioxabicyclo[2,2,2]oct-4-yl-methyl ester, 2,4-dichlorobenzoic acid 1-phospha-2,6,7-trioxabicyclo[2,2,2]oct-4-yl-methyl ester, p-octylbenzoic acid 1-phospha-2,6,7-trioxabicyclo[2,2,2]oct-4-yl-methyl ester, p-octadecyloxybenzoic acid 1-phospha-2,6,7-trioxabicyclo[2,2,2]oct-4-yl-methyl ester, p-acetoxybenozic acid 1-phospha-2,6,7-trioxabicyclo[2,2,2]oct-4-yl-methyl ester, p-stearyloxybenzoic acid 1-phospha-2,6,7-trioxabicyclo[2,2,2]oct-4-yl-methyl ester, p-methoxycarbonylbenzoic acid 1-phospha-2,6,7-trioxabicyclo[2,2,2]oct-4-yl-methyl ester, p-octadecyloxycarbonylbenzoic acid 1-phospha-2,6,7-trioxabicyclo[2,2,2]oct-4-yl-methyl ester, N-octadecylcarbamic acid 1-phospha-2,6,7-trioxabicyclo[2,2,2]oct-4-yl-methyl ester, N-benzylcarbamic acid 1-phospha-2,6,7-trioxabicyclo[2,2,2]oct-4-yl-methyl ester, N-m-methylphenylcarbamic acid 1-phospha-2,6,7-trioxabicyclo[2,2,2]oct-4-yl-methyl ester, N-p-tert.butylphenylcarbamic acid 1-phospha-2,6,7-trioxabicyclo[2,2,2]oct-4-yl-methyl ester, N-α-naphthylcarbamic acid 1-phospha-2,6,7-trioxabicyclo[2,2,2]oct-4-yl-methyl ester, oxalic acid di-1-phospha-2,6,7-trioxabicyclo[2,2,2]oct-4-yl-methyl ester, sebacic acid di-1-phospha-2,6,7-trioxabicyclo[2,2,2]oct-4-yl-methyl ester, terephthalic acid di-1-phospha-2,6,7-trioxabicyclo[2,2,2]oct-4-yl-methyl ester, and 2,6-naphthalenedicarboxylic acid di-1-phospha-2,6,7-trioxabicyclo[2,2,2]oct-4-yl-methyl ester.

The compounds of the formula I can be prepared by reacting an acid chloride of the formula II

(II)

with $n$ mols of the compound of the formula III

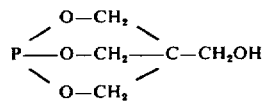
(III)

in the presence of a base to neutralise the hydrochloric acid which is formed.

A further process for preparation consists of reacting 1 mol of a carboxylic acid ester of the formula IV

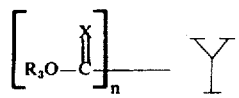
(IV)

wherein $R_3$ denotes a lower alkyl group, preferably methyl or ethyl, with $n$ mols of a compound of the formula III in the presence of a basic catalyst. In this reaction $n$ mols of $R_3OH$ are eliminated.

Examples of basic catalysts which are used are alkali metal amides, such as sodium amide or lithium amide, alkali metal hydroxides, such as lithium hydroxide, sodium hydroxide or potassium hydroxide, alcoholates, such as sodium alcoholates and magnesium alcoholates of methanol, ethanol or tert.butanol, or tertiary amines, such as triethylamine. Preferred basic catalysts are sodium methylate, sodium hydride and lithium amide.

A further process for preparation consists of reacting a pentaerythritol ester of the formula V

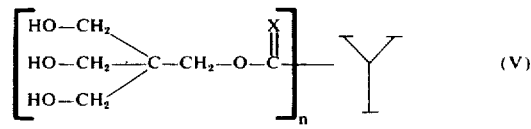
(V)

with $n$ mols of a compound of the formula VI

(VI)

wherein $R_4$ denotes methyl, ethyl or phenyl, preferably methyl, in the presence of a basic catalyst. In this reaction, $3\ n$ mols of $R_4OH$ are eliminated.

Alkali metal amides, alkali metal hydrides or alkali metal alcoholates are preferentially used as basic catalysts.

Compounds of the formula VII

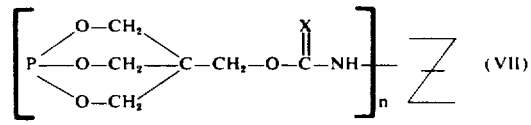
(VII)

in which $n$ and X have the meaning indicated under formula I and Z denotes alkyl with 1 to 18 carbon atoms, cyclohexyl, benzyl, phenyl, chlorophenyl, dichlorophenyl, alkylphenyl with 7–10 carbon atoms, naphthyl, alkylene with 2 to 9 carbon atoms, phenylene, toluylene, naphthylene or one of the radicals

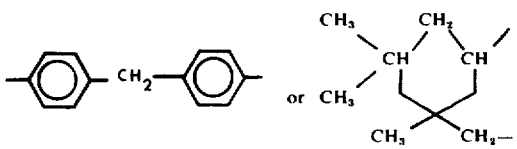

are prepared by reacting 1 mol of an isocyanate of the general formula VIII

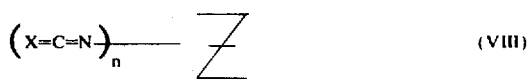
(VIII)

with $n$ mols of the compound of the formula III.

The reaction can be carried out in an aliphatic or aromatic hydrocarbon, such as benzine fractions, benzene, toluene or xylene as the solvent. It is preferably carried out without a solvent.

The compounds of the formula I protect polyolefines from degradation, for example polyolefines derived from hydrocarbons with single or double unsaturation, such as, for example, polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylene-propylene copolymers, propylene-butene-1 copolymers, propylene-isobutylene copolymers, styrene-butadiene copolymers and terpolymers of ethylene and propylene with a diene, such as, for example, hexadiene, dicyclopentadiene or ethylidene-norbornene; mixtures of the above-mentioned homopolymers, such as, for example, mixtures of polypropylene and polyethylene, polypropylene and polybutene-1, or polypropylene and polyisobutylene.

The above-mentioned homopolymers are preferably stabilised.

Preferably, 0.05 to 2.0, particularly preferably 0.1 to 1.0, % by weight of the compounds, relative to the material to be stabilised, are incorporated into the latter. The incorporation can be carried out, for example, by mixing in at least one of the compounds of the formula I and optionally further additives by the methods customary in the art, before or during moulding, or by applying the compounds, dissovled or dispersed, to the polymer, where appropriate with subsequent evaporation of the solvent.

In the case of crosslinked polyethylene, the compounds are added before the crosslinking.

The following may be mentioned as examples of further additives with which the stabilisers can be conjointly employed:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as, for example, 2,5-di-tert.-butyl-hydroquinone, 2,5-di-tert.-amyl-hydroquinone, 2,6-di-tert.-butyl-hydroquinone, 2,5-di-tert.-butyl-4-hydroxy-anisole, 3,5-di-tert.-butyl-4-hydroxy-anisole, tris-(3,5-di-tert.-butyl-4-hydroxyphenyl)-phosphite, 3,5-di-tert.-butyl-4-hydroxyphenyl-stearate and bis-(3,5-di-tert.-butyl-4-hydroxyphenyl)-adipate.

1.3 Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.

1.4 Alkylidene-bisphenols, such as, for example, 2,2'-methylene-bis-(6-tert.butyl-4-methylphenol),2,2'-methylene-bis-(6-tert.butyl-4-ethylphenol), 4,4'-methylene-bis-(6-tert.butyl-2-methylphenol), 4,4'-methylene-bis-(2,6-di-tert.butyl-phenol), 2,6-di-(3-tert.butyl-5-methyl-2-hydroxybenzyl)-4-methyl-phenol, 2,2'-methylene-bis-[4-methyl-6-(α-methylcyclohexyl)-phenol], 1,1-bis-(3,5-dimethyl-2- hydroxyphenyl)butane, 1,1-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecylmercapto-butane, 1,1,5,5-tetra-(5-tert.butyl-4-hydroxy-2-methylphenyl)-pentane and ethyleneglycol-bis-[3,3-bis-(3'-tert.butyl-4'-hydroxyphenyl)-butyrate].

1.5 O-, N- and S-benzyl compounds, such as, for example, 3,5,3',5'-tetra-tert.butyl-4,4'-dihydroxydibenzyl ether, 4-hydroxy-3,5-dimethylbenzyl-mercaptoacetic acid octadecyl ester, tris-(3,5-di-tert.butyl-4-hydroxybenzyl)-amine and bis-(4-tert.butyl-3-hydroxy-2,6-dimethylbenzyl)-dithioterephthalate.

1.6 Hydroxybenzylated malonic esters, such as, for example, 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert.butyl-4-hydroxybenzyl)-malonic acid di-dodecylmercapto-ethylester and 2,2-bis-(3,5-di-tert.butyl-4-hydroxybenzyl)-malonic acid di-[4-(1,1,3,3-tetramethylbutyl)-phenyl]-ester.

1.7 Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8 s-Triazine compounds, such as, for example, 2,4-bis-octylmercapto-6-(3,5-di-tert.butyl-4-hydroxyanilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9 Amides of β-(3,5-di-tert.butyl-4-hydroxyphenyl)-propionic acid, such as, for example, 1,3,5-tris-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.10. Esters of β-(3,5-di-tert.butyl-4-hydroxyphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.11. Esters of β-(5-tert.butyl-4-hydroxy-3-methylphenyl propionic acid with monohydric or polyhydric alcohols such as, for example, methanol, ethanol, octadecanol, 1,6-hexanediol, 1,91.11. ethylene glycol, 1,2-propanediol, diethylene glycol, thiodiethylene glycol, neopentyl glycol, pentaerythritol, 3-this-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.12. Esters of 3,5-di-tert.butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.13. Acylaminophenols, such as, for example, N-(3,5-di-tert.butyl-4-hydroxyphenyl)-stearic acid amide and N,N'-di-(3,5-di-tert.butyl-4-hydroxyphenyl)-thiobis-acetamide.

1.14. Benzylphosphonates, such as, for example, 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.15. Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N-sec.octyl-p-phenylenediamine, N,N'-di-(1,4-dimethylpentyl)-p-phenylenediamine, N,N'-dimethyl-N,N'-di-(sec.octyl)-p-phenylenediamine, 2,6-dimethyl-4-methoxyaniline, 4-ethoxy-N-sec.-butylaniline, the condensation product of diphenylamine and acetone, and phenothiazine.

2. UV absorbers and light protection agents 2.1. 2-(2'-Hydroxyphenyl)-benztriazoles, such as, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.amyl-, 3'-methyl-5'-carbomethoxyethyl- and 5-chloro-3',5'-di-tert.-amyl-derivative.

2.2. 2,4-Bis-(2'-hydroxyphenyl)-6-alkyl-s-triazines, such as, for example, the 6-ethyl-, 6-heptadecyl or 6-undecyl-derivative.

2.3. 2-Hydroxy-benzophenones, such as, for example, the 4-hydroxy-, 4-methoxy-, 4-octoxy-, 4-decyloxy-, 4-dodecyloxy-, 4-benzyloxy, 4,2',4'-trihydroxy- or 2'-hydroxy-4,4'-dimethoxy-derivative.

2.4. 1,3-Bis-(2'-hydroxy-benzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids such as, for example, phenyl salicylate, octylphenyl salicylate, dibenzoylresorcinol, bis-(4-tert.-butylbenzoyl)-resorcinol, benzoyl-resorcinol and 3,5-di-tert.-butyl-4-hydroxybenzoic acid 2,4-di-tert.butyl-phenyl ester, octadecyl ester or 2-methyl-4,6-di-tert.butyl-phenyl ester.

2.6. Acrylates, such as, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxy-vinyl)-2-methyl-indoline.

2.7. Nickel compounds, such as, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel complexes of bis-[2-hydroxy-4-(1,1,3,3-tetramethylbutyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert.butylbenzyl-phosphonic acid monoalkyl esters, such as of the methyl, ethyl or butyl ester, nickel complexes of ketoximes such as of 2-hydroxy-4-methyl-phenyl-undecylketonoxime, nickel 3,5-di-tert.butyl-4-hydroxy-benzoate and nickel isopropylxanthate.

2.8. Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl) sebacate, and 3-n-octyl-7,7,9,9-tetramethyl-1,3,8-triaza-spiro[4,5]decane-2,4-dione.

2.9. Oxalic acid diamides, such as, for example, 4,4'-di-octyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyl-oxanilide and its mixture with 2-ethoxy-2'-ethyl-5,4'-di-tert.butyl-oxanilide and mixtures of ortho- and para-methoxy- as well as of o- and p-ethoxy-disubstituted oxanilides.

3. Metal deactivators, such as, for example, oxanilide, isophthalic acid dihydrazide, sebacic acid bis-phenyl-hydrazide, bis-benzylidene-oxalic acid dihydrazide, N,N'-diacetyl-adipic acid dihydrazide, N,N'-bis-salicyloyloxalic acid dihydrazide, N,N'-bis-salicyloyl-hydrazine, N,N'-bis-(3,5-di-tert.butyl-4-hydroxyphenyl-propionyl)-hydrazine, N-salicylal-N-salicylidenehydrazine and 3-salicyloylamino-1,2,4-triazole.

4. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-di-isodecyloxy-2,4,8,10-tetraoxa-3,9-diphosphaspiro[5,5]undecane and tri-(4-hydroxy-3,5-di-tert.butylphenyl) phosphite.

5. Compounds which destroy peroxides, such as, for example, esters of β-thiodipropionic acid, for example the lauryl, stearyl, myristyl or tridecyl esters, mercapto-benzimidazole and the zinc salt of 2-mercapto-benzimidazole.

6. Polyamide stabilisers, such as, for example, copper salts in combination with iodides and/or phosphorus compounds and salts of divalent manganese.

7. Basic co-stabilisers, such as, for example, melamine, benzoguanamine, polyvinylpyrrolidone, dicyandiamide, triallyl cyanurate, urea derivatives, hydrazine derivatives, amines, polyamides, polyurethanes, and alkali metal salts and alkaline earth metal salts of higher fatty acids, for example Ca stearate, Zn stearate, Mg stearate, Na ricinoleate, K palmitate, antimony pyrocatecholate or zinc pyrocatecholate.

8. PVC stabilisers, such as, for example, organic tin compounds, organic lead compounds and barium-cadmium salts of fatty acids.

9. Nucleating agents, such as for example 4-tert.butyl-benzoic acid, adipic acid and diphenylacetic acid.

10. Urea derivatives, such as, for example, N-cyclohexyl-N'-1-naphthylurea, N-phenyl-N,N'-dicyclohexylurea, N-phenyl-N'-2-naphthylurea, N-phenylthiourea, N,N'-dibutylthiourea.

11. Other additives, such as, for example, plasticisers, lubricants, emulsifiers, fillers, carbon black, asbestos, kaolin, talc, glass fibres, pigments, optical brighteners, flameproofing agents and antistatic agents.

The preparation and use of the compounds according to the invention are described in greater detail in the examples which follow. In these, parts denote parts by weight and % denotes percentages by weight.

EXAMPLE 1

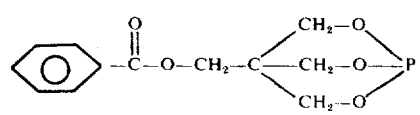

16.4 g (0.1 mol) of 4-hydroxymethyl-1-phospha-2,6,7-trioxabicyclo[2,2,2]octane are dissolved in 150 ml of toluene by warming. 19.6 g (0.1 mol) of benzoyl chloride are added dropwise at room temperature, followed by 10.1 g (0.1 mol) of triethylamine. The temperature is kept at 30 C by means of an ice bath. After the dropwise addition is complete, the mixture is stirred for 2 hours at 60°C and is then heated to the boil for a short time and filtered while hot from triethylamine hydrochloride. The filtrate is cooled, whereupon the product is precipitated. After filtering and drying, benzoic acid 1-phospha-2,6,7-trioxabicyclo[2,2,2]oct-4-yl-methyl ester (Stabiliser No. 1) of melting point 160°C is obtained. After recrystallisation from ethanol or isopropanol the product forms long, snow-white needles. If in this example, the benzoyl chloride is replaced by an equivalent quantity of one of the substituted benzoic acid chlorides in Table 1 below, an otherwise identical procedure gives benzoic acid 1-phospha-2,6,7-trioxabicyclo[2,2,2]oct-4-yl methyl esters substituted at the nucleus, the melting points of which are shown.

16.4 g (0.1 mol) of 4-hydroxymethyl-1-phospha-2,6,7-trioxabicyclo[2,2,2]octane are dissolved in 150 ml of toluene by warming. 30.2 g (0.1 mol) of stearic acid chloride, followed by 10.1 g (0.1 mol) of triethylamine, are added dropwise at room temperature. After the slight evolution of heat has died away, the mixture is stirred for 10 hours under nitrogen at room temperature and the precipitated triethylamine hydrochloride is then filtered off. The filtrate is evaporated with exclusion of moisture, a yellowish oil remaining, which crystallises on being triturated with methanol. After filtering off under suction and drying, stearic acid 1-phospha-2,6,7-trioxabicyclo[2,2,2]oct-4-yl-methyl ester (Stabiliser No. 9), melting point 49°C, is obtained.

If, in this example, the stearic acid chloride is replaced by an equivalent quantity of one of the aliphatic or araliphatic carboxylic acid chlorides in Table 2 below, an otherwise identical procedure gives the corresponding 1-phospha-2,6,7-trioxabicyclo[2,2,2]oct-4-yl-methyl esters the melting points of which are shown.

Table 1

| Acid chloride | Melting point of the reaction product | Stabiliser No. |
|---|---|---|
| 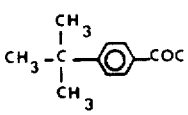 | 158°C | 2 |
| 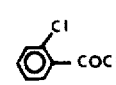 | 97°C | 3 |
| 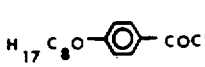 | 96°C | 4 |
| 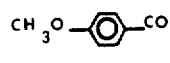 | 137°C | 5 |
|  | 176°C | 6 |
|  | 173°C | 7 |
| 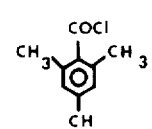 | 82°C | 8 |

EXAMPLE 2

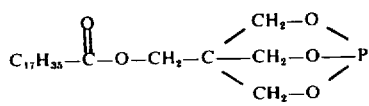

Table 2

| Acid chloride | Melting point of the reaction product | Stabiliser No. |
|---|---|---|
| CH₃—C(CH₃)(CH₃)—COCl | 124°C | 10 |

Table 2-continued

| Acid chloride | Melting point of the reaction product | Stabiliser No. |
|---|---|---|
| 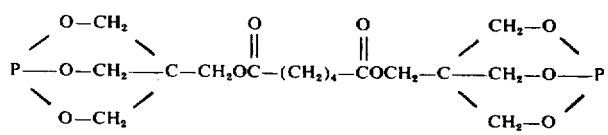 | 82°C | 11 |

EXAMPLE 3

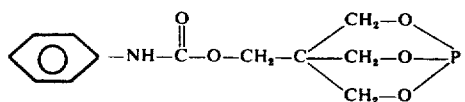

32.8 g (0.2 mol) of 4-hydroxymethyl-1-phospha-2,6,7-trioxabicyclo[2,2,2]octane are mixed with 17.4 g (0.1 mol) of adipic acid dimethyl ester, the mixture is heated to 60°C with stirring and 1.0 g of Na methylate are added. The temperature is slowly brought up to 120°C, methanol distilling off. After the reaction has subsided, the mixture is heated to 145°C, the reaction vessel is evacuated and the mixture is stirred for a further hour. The yellowish melt is cooled and 100 ml of absolute alcohol are added, whereupon the product crystallises.

After filtration and drying, adipic acid di-1-phospha-2,6,7-trioxabicyclo[2,2,2]oct-4-yl-methyl ester (Stabiliser No. 12), melting point 120°C, is obtained.

If, in this example, the adipic acid dimethyl ester is replaced by an equimolecular quantity of succinic acid dimethyl ester, an otherwise identical procedure gives succinic acid di-1-phospha-2,6,7-trioxabicyclo[2,2,2]oct-4-yl-methyl ester (Stabiliser No. 13), melting point 130°C.

EXAMPLE 4

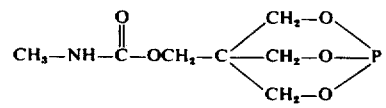

32.8 g (0.2 mol) of 4-hydroxymethyl-1-phospha-2,6,7-trioxabicyclo[2,2,2]octane are melted at 60°C and 23.8 g (0.2 mol) of phenylisocyanate are added, a homogeneous, colourless melt being formed. The temperature of the melt is brought up to 90°C, whereupon the contents of the flask solidify within 15 minutes. The temperature is kept at 90°C for a further half hour and the mixture is then cooled and the product is recrystallised from absolute ethanol. N-Phenylcarbamic acid 1-phospha-2,6,7-trioxabicyclo[2,2,2]oct-4-yl-methyl ester (Stabiliser No. 14), with a melting point of 172°C, is thus obtained.

If, in this example, the phenylisocyanate is replaced by an equivalent quantity of 4-chlorophenylisocyanate, an otherwise identical procedure gives N-(4-chlorophenyl)-carbamic acid 1-phospha-2,6,7-trioxabicyclo[2,2,2]-oct-4-yl-methyl ester.

EXAMPLE 5

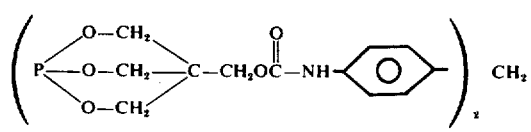

If the procedure of Example 4 is repeated using 32.8 g (0.2 mol) of 4-hydroxymethyl-1-phospha-2,6,7-trioxabicyclo[2,2,2]octane and (0.1 mol) of 4,4'-diphenylmethanediisocyanate at a reaction temperature of 120°C, 4,4'-diphenylmethanedicarbamic acid di-1-phsopha-2,6,7-trioxabicyclo[2,2,2]oct-4-yl-methyl ester (Stabiliser No. 15), melting point 238°C, is obtained. If 4,4'-diphenylmethanediisocyanate is replaced by an equivalent quantity of toluylene-2,4-diisocyanate, an otherwise identical procedure gives toluylene-2,4-dicarbamic acid di-1-phospha-2,6,7-trioxabicyclo[2,2,2]oct-4-yl-methyl ester, with a melting point of 235°C. (Stabiliser No. 16).

EXAMPLE 6

16.4 g (0.1 mol) of 4-hydroxymethyl-1-phospha-2,6,7-trioxabicyclo[2,2,2]octane and 5.7 g (0.1 mol) of methylisocyanate are sealed in a bomb tube and are heated at 120°C for 15 hours. On cooling, the contents of the tube solidify. The N-methylcarbamic acid 1-phospha-2,6,7-trioxabicyclo[2,2,2]oct-4-yl-methyl ester (Stabiliser No. 17) obtained has a melting point of 98°C after recrystallisation from toluene.

If, in this example, the methylisocyanate is replaced by an equivalent quantity of the aliphatic monoisocyanates or diisocyanates in Table 3 below, anotherwise identical procedure gives the N-substituted carbamic acid 1-phospha-2,6,7-trioxabicyclo[2,2,2]oct-4-yl-methyl esters with the melting points or boiling points which are shown:

Table 3

| Isocyanate | Reaction product | Stabiliser No. |
|---|---|---|
| C₄H₉—NCO | Boiling point 192°C/2 mm | 18 |
| (phenyl)—NCO | Boiling point 150°C | 19 |
| OCN—(CH₂)₆—NCO | Viscous oil | 20 |
| OCN-isoC₉H₁₈—NCO | Viscous oil | 21 |
| (tricyclic structure with CH₂NCO) | Viscous oil | 22 |

EXAMPLE 7

Stabilisation of polyproylene against thermo-oxidative degradation during processing The stabilisers in Table 4 below are homogeneously mixed in a concentration of 0.1% with polypropylene powder ("Propathene HF 20" of Messrs. ICI) and are re-granulated 5 times successively in a single-screw extruder at a die temperature of 260°C and at 100 rpm. The melt index of the material is measured in each case after the 1st, 3rd and 5th extrusion (2160 g load at 230°C, g/10 min.). An experiment containing no stabiliser of any sort is used as a comparison. A degradation of the polymer manifests itself by a rapid increase in the melt index.

Table 5-continued

| Stabiliser No. | State as received | Melt index After 1 extrusion | After 3 extrusions | After 5 extrusions |
|---|---|---|---|---|
| 6 | 2.5 | 3.6 | 5.5 | 7.8 |
| 19 | 2.5 | 3.8 | 6.1 | 7.4 |

EXAMPLE 9

The stabilisers listed in Table 6 below are put in crystallising dishes of 44.2 $cm^2$ area as a layer 1 cm high, (a) as the pure, crystalline substance and (b) as an intimate mixture with an equal weight of zinc stearate. The stabiliser samples are conditioned for 19 days at 20°C and 80% relative humidity. The absorption of water is measured periodically by weighing and is expressed as a percentage of the initial weight.

Table 6

| Stabiliser No. | Percentage increase in weight after days | | | | | | | | | | |
|---|---|---|---|---|---|---|---|---|---|---|---|
|  | 1 | 2 | 5 | 6 | 8 | 9 | 12 | 13 | 14 | 16 | 19 |
| 2 | 0 | 0 | 0 | 0 | 1.2 | 2.1 | 8.3 | 10.8 | 13.7 | 19.5 | 26.8 |
| 2 + equal quantity of zinc stearate | 0 | 0 | 0 | 0 | 0.03 | 0.02 | 8.16 | 0.22 | 0.28 | 0.37 | 0.56 |
| 19 | 0 | 0.4 | 4.3 | 5.6 | 9.4 | 10.8 | 17 | 19 | 21 | 25.6 | 30.1 |
| 19 + an equal quantity of zinc stearate | 0 | 0 | 0 | 0 | 0 | 0 | 0 | 0 | 0 | 0 | 0 |

It can be seen from Table 6 that the addition of zinc stearate to the Stabilisers Nos. 2 and 19 suppresses their susceptibility to hydrolysis.

Table 4

| Stabiliser No. | State as received | Melt index After 1 extrusion | After 3 extrusions | After 5 extrusions |
|---|---|---|---|---|
| — | 2.5 | 7.0 | 13.9 | 36 |
| 2 | 2.5 | 2.6 | 5.5 | 6.4 |
| 4 | 2.5 | 4.0 | 9.8 | 20 |
| 13 | 2.5 | 4.2 | 10.5 | 22 |
| 17 | 2.5 | 4.8 | 7.8 | 13.8 |
| 19 | 2.5 | 3.4 | 5.2 | 8.4 |

EXAMPLE 8

Stabilisation of polypropylene against thermo-oxidative degradation during processing 0.05% of pentaerythritol-tetrakis-[3-(3',5'-di-tert.butyl-4-hydroxyphenyl)]-propionate and 0.05% of a stabiliser in Table 5 below are each homogeneously mixed with polypropylene powder ("Propathene HF 20" of Messrs. ICI) and are re-granulated 5 times successively in a single-screw extruder at a die temperature of 260°C and at 100 rpm. The melt index of the material is measured in each case after the 1st, 3rd and 5th extrusion (2160 g load at 230°C, g/10 min.). An analogous experiment with a powder mixture containing only 0.05% of pentaerythritol-tetrakis[3-(3',5'-ditert.butyl-4-hydroxyphenyl)]-propionate is used as a comparison. A degradation of the polymer manifests itself by a rapid increase in the melt index.

Table 5

| Stabiliser No. | State as received | Melt index After 1 extrusion | After 3 extrusions | After 5 extrusions |
|---|---|---|---|---|
| — | 2.5 | 5.6 | 10.0 | 12.3 |
| 2 | 2.5 | 3.3 | 4.6 | 9.4 |
| 9 | 2.5 | 4.3 | 5.6 | 9.0 |

EXAMPLE 10

0.1 of one of the Stabilisers Nos. 1 to 22 and 0.1 part of a stabiliser in Table 7 below are each homogeneously mixed with 100 parts of polypropylene powder ("Propathene HF20" of Messrs. ICI) and are kneaded for 10 minutes in a Brabender plastograph at 200°C. The composition obtained in this way is then pressed into sheets 1 mm thick in a plate press at a plate temperature of 260°C. The comparison samples, which contain only 0.1 part of a stabiliser in Table 7, are prepared in an analogous manner.

The samples are assessed visually in respect of their discolouration during the process of incorporation. This shows that the discolourations which occur to a greater or less pronounced extent as a result of the stabilisers in Table 7, are virtually completely suppressed by the Stabilisers Nos. 1–22.

TABLE 7

2,6-Ditert.butyl-4-methylphenol
1,3,5-Tris-(3,5-ditert.butyl-4-hydroxyphenyl)-isocyanate
Octadecyl-3,5-ditert.butyl-4-hydroxyphenyl-propionate
Pentaerythritol-tetrakis-[3-(3',5'-ditert.butyl-4-hydroxyphenyl)]-propionate
Dioctadecyl-3,5-ditert.butyl-4-hydroxyphenyl-phosphonate
Diethyl-3,5-ditert.butyl-4-hydroxyphenyl-phosphonate
1,1,3-Tris-(5-tert.butyl-4-hydroxy-2-methylphenyl)-butane
1,3,5-Tris-(3,5-ditert.butyl-4-hydroxybenzyl)-2,4,6-trimethylbenzene.

EXAMPLE 11

100 parts of crystal polystyrene granules are mixed dry with 0.25 part of a stabiliser in Table 8 which follows, are re-granulated in an extruder and are then injection-moulded to give sheets 2 mm thick by means of an injection moulding machine. The sheets obtained are exposed for 3,000 hours in a "Xenotest 150" exposure apparatus and their yellowing after 2,000 and 3,000 hours is determined in the following way by means of the "yellowing factor":

$$\text{Yellowing factor (Y.F.)} = \frac{\Delta T\,420 - \Delta T\,680}{T\,560}$$

$\Delta T$ denoting the loss in transmission which has occurred during the exposure at wavelengths of 420 or 680 mm and T 560 denoting the transmission index of the unexposed sample at 560 mm.

Table 8

| Stabiliser No. | Yellowing factor after hours Xenotest 150 | |
|---|---|---|
| | 2,000 | 3,000 |
| None | 28.1 | 43.9 |
| 2 | 16.8 | 26.9 |

EXAMPLE 12

100 parts of crystal polystyrene granules are mixed dry with 0.15 part of 2-(2'-hydroxy-5'-methylphenyl)-benztriazole and 0.1 part of a stabiliser in Table 9 which follows, and are re-granulated in an extruder and subsequently injection-moulded to give sheets 2 mm thick by means of an injection-moulding machine. The sheets obtained are exposed for 3,000 hours in a "Xenotest 150" exposure apparatus and their yellowing after 2,000 and 3,000 hours is determined in the following manner by means of the "yellowing factor":

$$\text{Yellowing factor (Y.F.)} = \frac{\Delta T\,420 - \Delta T\,680}{T\,560}$$

$\Delta T$ denoting the loss in transmission which has occurred during the exposure at wavelengths of 420 or 680 mm and T 560 denoting the transmission index of the unexposed sample at 560 mm.

Table 9

| Stabiliser No. | Yellowing factor after hours Xenotest 150 | |
|---|---|---|
| | 2,000 | 3,000 |
| None | 19.1 | 30.3 |
| 2 | 4.4 | 21.3 |
| 19 | 1.1 | 12.3 |

We claim:

1. A compound of the formula I,

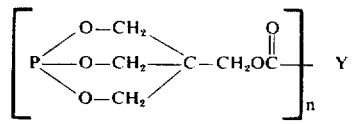

characterised in that $n$ denotes 1 or 2, Y denotes, if $n$ is equal to 1, alkylamino with 1–18 carbon atoms, cyclohexylamino, benzylamino, anilino, chloroanilino, dichloroanilino, alkylanilino with 7–10 carbon atoms or naphthylamino, or, if $n$ is equal to 2, alkylenediamino with 2–9 carbon atoms, phenylenediamino, toluylenediamino, naphthylenediamino, diphenylmethane-4,4'-diamino or the radical

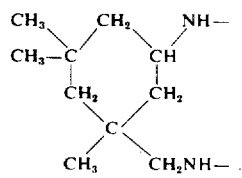

2. A compound according to claim 1 of the formula I, characterised in that $n$ denotes 1, Y denotes alkylamino with 1–18 carbon atoms, cyclohexylamino, anilino, chloroanilino or naphthylamino.

3. A compound according to claim 1 of the formula I, characterised in that $n$ denotes 1 or 2, Y denotes, if $n$ is equal to 1, alkylamino with 1–4 carbon atoms or anilino, or, if $n$ is equal to 2, alkylenediamino with 6–9 carbon atoms, diphenylmethane-4,4'–diamino 2,4-toluenediamino or the radical

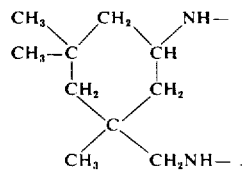

* * * * *